(12) United States Patent
Pushpangadan et al.

(10) Patent No.: US 7,014,872 B2
(45) Date of Patent: Mar. 21, 2006

(54) HERBAL NUTRACEUTICAL FORMULATION FOR DIABETICS AND PROCESS FOR PREPARING THE SAME

(75) Inventors: Palpu Pushpangadan, Lucknow (IN); Dhan Prakash, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 20 days.

(21) Appl. No.: 10/108,095

(22) Filed: Mar. 26, 2002

(65) Prior Publication Data

US 2003/0185913 A1    Oct. 2, 2003

(51) Int. Cl.
*A61K 35/78*   (2006.01)

(52) U.S. Cl. ............... 424/725; 424/734; 424/757; 424/739; 424/756

(58) Field of Classification Search ............... 424/725, 424/734, 757, 739, 756
See application file for complete search history.

(56) References Cited

U.S. PATENT DOCUMENTS 5,866,555 A * 2/1999 Bell et al.
5,886,029 A * 3/1999 Dhaliwal
2002/0025349 A1 * 2/2002 Brindavanam et al.

OTHER PUBLICATIONS

Andallu et al. (Indian Journal of Experimental Biology (2000), vol. 38, No. 6, pp. 607-609).*
Choi et al. (Journal of Food Science and Nutrition (1998), vol. 3, No. 4, pp. 356-361).*
Mehio et al (Journal of Nutritional and Environmental Medicine (1997), vol. 7, pp. 275-286).*
Mesa et al. (Recent Research Developments in Nutrition Research (2000), vol. 3, pp. 157-171).*
Platel et al. (Die Nahrung (1997), vol. 41, No. 2, pp. 68-74).*
Rana et al. (Journal of Economic and Taxonomic Botany (1999), vol. 23, No. 1, pp. 115-120).*
www.diabetes.org, accessed Jul. 26, 2004.*

* cited by examiner

*Primary Examiner*—Susan D. Coe
(74) *Attorney, Agent, or Firm*—RatnerPrestia

(57) ABSTRACT

The present invention relates to a herbal health protective, promotive and disease preventive nutraceutical herbal formulation(s) for diabetics, and also relates to a process for the preparation of a herbal health protective, promotive and disease preventive nutraceutical herbal formulation as food supplement to ameliorate the general health of diabetics, said formulation comprises the base product of microwave roasted seed powders mixture from selected genera of *Glycine, Cicer, Phaseolus, Cyamompsis, Mucuna, Hordeum, Amaranthus* and *Fagopyrum*, fortified with herbs/medicinal plants used are selected from the genera of *Gymnema, Momordica, Syzgium, Pterocarpus, Trigonella, Cinnamomum, Withania, Coccinia, Pueraria, Asparagus, Boerhaavia* and *Aegle* and also some other ingredients like *Piper longum, Chlorophytum tuberosum, Curcuma longa* and *Elettaria cardamomum* were also added to get the final nutraceutical product(s); the nutraceuticals are with optimum nutrition, non toxic, natural herbal plant products, easy to digest, have health protective and promotive properties to ameliorate the general health and vigor of diabetics.

22 Claims, No Drawings

HERBAL NUTRACEUTICAL FORMULATION FOR DIABETICS AND PROCESS FOR PREPARING THE SAME

FIELD OF THE INVENTION

The present invention relates to an herbal health protective and promotive nutraceutical formulations to ameliorate the general health of diabetics.

BACKGROUND OF THE INVENTION

The nutraceutical food or parts of food may provide medical health benefits including the prevention and or treatment of diseases. Nutraceuticals, are foods or bioactive ingredients in foods that protect or promote health whether delivered in raw agricultural commodities, processed foods, dietary supplements, extracts, beverages or other products and occurs at the intersection of food and pharmaceutical industries. The development of next generation nutraceutical "super foods" or products consist value-addition in the traditional natural diets. Their ingredients have tremendous impact on the health care system and may provide medical health benefits including the prevention and or treatment of diseases. Nutraceuticals have potential to be used as food supplement, preventive medicine and the growing evidence points in the direction that certain foods fight and or prevent against diseases.

The word Nutraceuticals combine 'nutrition' and 'pharmaceuticals' to mean that they can be used as preventive drugs or food supplements. The entire concept is based on the disease preventing/treating phytonutrients present in foodstuffs of the diet in combating diseases e.g. phytosterols compete with dietary cholesterol for uptake in intestine thereby blocking cholesterol absorption into the body and can also prevent the development of tumor in breast and prostate glands. Phenols a large group of phytonutrients, have profound importance in preventive medicine. Phytochemicals can enhance the efficacy of vitamin C, can also act against allergies, ulcers, tumors, platelet aggregation, controlling hypertension and reduce the risk of estrogen induced cancer.

The food plays significant role in the general health of diabetics, heart, nerves and aged. The right foods do have the power to heal, keeping good health of body functions, ageing, rejuvenating, immuno-modulating and prevention against diseases, just as the wrong foods can cause sickness, rapid ageing and premature death.

DESCRIPTION OF THE PRIOR ART

Reference is made to a book by Balch P A & Balch J F (Rx Prescription for Dietary Wellness, 1993, USA) wherein importance of phytochemicals, protease inhibitors from legumes against tumor growth and ability to block natural carcinogens from forming tumors have been mentioned. Whole grains, germinated seeds, legumes and herbs are basically powerful foods. Reference is made to books by Guha Bakshi D N, Sensarma P & Pal D C (A Lexicon of Medicinal Plants in India, Naya Prokash, 1999, Calcutta, India); Chopra R N, Nayar S L, & Chopra I C (Glossary of Indian Medicinal Plants, NISCOM, CSIR, New Delhi, India 1999); Anonymous (Wealth of India, Raw Materials, CSIR, New Delhi, India) and a chapter Seed Proteins by Prakash D (Current Concepts in Seed Biology K G Mukerji et al. Eds 1993); published research articles by Misra P S, Prakash D, Pandey R M & Pal M, Fitoterapia 56: 318–320, 1985; Prakash D, Narayan P & Misra P S, Plant Foods Hum. Nutr. 36: 341–344, 1987; Prakash D & Pal M, J. Sci. Food Agric. 58: 145–147, 1992; Prakash D, Joshi B D & Pal M, Int. J. Food Sci. Nutr. 46: 47–51, 1995; Prakash D, Niranjan A & Tewari S K Int. J. Food Sci. Nutr. 52: 79–82, 2001) wherein the significant nutritional composition, traditional medicinal and pharmaceutical uses of soybean (*Glycine max*), chickpea (*Cicer arietinum*), black-gram/'Urd' (*Phaseolus mungo*), 'Guar' (*Cyamopsis tetragonoloba*), 'Kewanch' (*Mucuna pruriens*), barley (*Hordeum vulgare*), amaranth (*Amaranthus hypochondriacus*) and buckwheat (*Fagopyrum esculantus*) have been described. Their seeds are being used as edible foods in the form of different kind of preparations without fortification with herbs/medicinal plants. Reference is made to books by Chaudhri R D (Herbal Drugs Industry, Eastern Publishers, 1996, New Delhi); Guha Bakshi D N, Sensarma P & Pal D C (A Lexicon of Medicinal Plants in India, Naya Prokash, 1999, Calcutta, India); Chopra R N, Nayar S L, & Chopra I C (Glossary of Indian Medicinal Plants, NISCOM, CSIR, New Delhi, India 1999); Kapoor L D (Handbook of Ayurvedic Medicinal Plants, CRC Press, Florida, 1990); Sharma P V (Dravyaguna Vijnana, Vol II, 1992, Chaukhambha Bharati Academy, Varanasi); Balch P A & Balch J F (Rx Prescription for Dietary Wellness, 1993, USA) and Anonymous (Wealth of India, Raw Materials, CSIR, New Delhi, India) wherein the traditional and modem medicinal uses of the herbs/medicinal plants like *Gymnema sylvestre, Momordica charantia, Syzgium cumini, Pterocarpus marsupium, Trigonella foenum-graecum, Cinnamomum tamala, Withania somnifera, Coccinia indica, Pueraria tuberosa, Asparagus racemosus, Boerhaavia diffusa, Aegle marmelos, Piper longum, Chlorophytum tuberosum, Curcuma longa* and *Elettaria cardamomum* have been mentioned. These herbs/medicinal plants are being used for the preparation of different kind of medicines alone or in different combinations/formulations.

A number of patents have been granted on nutraceuticals, which comprises either a single or a mixture of several phytonutrients in various concentrations. In some cases, the products were even fortified with synthetic ingredients also. Reference is made to patents (Patent No. AU2557899; WO9935917) wherein methods of infusing phytochemicals, nutraceuticals and other compositions into food products e.g. juices, fruits, vegetables and meats, etc through osmotic dehydration are described. The methods are tedious including the use of some chemicals during the preparation. Reference is made to patents (Patent No. AU4777100; WO0064282) wherein nutraceuticals and ingredients for functional foods are prepared by co-spray drying using fructans, fructooligosaccharides instead of maltodextrins as a drying agent and ingredients such as flavonoids, anthocyanins, resveratrol. The main emphasis has been limited to phenolic phytochemicals and products are in the form of a gel or cream, showing fat like texture, which can only be used as spreader. Reference is made to patents (Patent No. AU4038800; WO0057726) wherein nutraceuticals comprising a blend of N-[N-(3,3-dimethylbutyl)-L-alpha-aspartyl]-L-phenylalanine 1-methyl ester (neotame) with another sweetener has been mentioned. The compounds used are synthetic and have limited importance only as sweetener or flavor modifier in nutraceuticals. Neotame is a synthetic variation of aspartame and poses potential major health problems like incidents of grand mal seizures, brain tumors and environmental hazards. Reference is made to patents (U.S. Pat. No. 6,087,353; AU3696599; WO9959421) wherein esterified and subsequently hydrogenated phytosterol composition for use alone or for incorporation into foods, beverages, pharmaceuticals and nutraceuticals have been described. The isolated phytosterols from plants have been modified by chemical process of esterification for the physical characteristics. Reference is made to patent (U.S. Pat. No. 6,099,867) wherein a nutraceutical composition comprising water insoluble or water soluble antler powder or a combination and method of producing the same has been described. The products are non-ecofriendly of animal origin with limited nutraceutical importance. Reference is made to patent (U.S. Pat. No. 6,093,403) wherein sugar imbalance and diabetes treating herbal formulation in lectin prepared from Chinese herbs has been described. The formulation has been reported to lower the blood glucose and insulin levels but without nutraceutical benefits in NIDDM.

The use of plant extracts and derivatives of plants for healing and prevention purposes has been described extensively in traditional and folk medicine literature. Over the centuries, plants have served as a major source of medicines for treating and prevention of diseases of mankind. Although recently the ability for synthesis and design of new medicines has provided new pathways for the development of therapeutic drugs, however, phytomedicines derived from plants still hold strong position. Indigenous foods in the treatment of diabetes mellitus have been described by G Subbulakshmi & Mridula Naik (SNDT Women's University, Mumbai, Internet). For centuries, specific plants, their extracts or mixtures thereof have been used for treatment of illnesses in Indian system of medicine and many of them have been documented as having clinical effectiveness in treating illnesses. The plants like Alfalfa, Aloe vera, Burdock, Celery, Cornsilk, Damiana, Elecampane, Eucalyptus, Fenugreek, Garlic, Ginger, Ginseng, Panax, Juniper, Marshmallow, Myrrh, Nettle, Sage, Tansy have been reported as hypoglycemic herbal ingredients (Internet). Commercial products with branded names such as Pancreas Formula, Eleotin, Ayubes, Diabetes Hypoglucose Capsules, Pearl Hypoglycemic Capsules, Tongyitang Diabetes Angle Hypoglycemic Capsules, Zhen Qi Capsules are available in internationational market on internet. In India commercial products available in market are Cogent-db, Diabyog Capsules, Diabyog Granules, Diabecon, Madhu Mehari Granules, Madhu Sunya and Madhumeh Amrit etc. Most of the products (a list given in Table 1) are a mixture of herbs/medicinal plants, minerals, and bhasams (ashes) without a suitable balanced nutritional composition to ameliorate the general health of diabetics and none of them is a nutraceutical. Nutraceuticals with different branded names are commercially available in international (Internet) and Indian market. Besides the natural ingredients majority of the products also contains some synthetic ingredients and recommended as food supplement for nutrition only. While, the present invention provides a process for the preparation of nutraceuticals with specific combination of edible legumes, cereals, pseudocereals for natural nutrients and herbs/medicinal plants with significant medicinal values to provide optimum balanced nutrition and general health protective, promotive and disease preventive benefits to the diabetics. To the best of the Applicant's knowledge no nutraceutical comprising a combination of legumes, cereals, pseudocereals fortified with herbs/medicinal plants used in the present invention or a process for the preparation of the same exist for diabetic patients.

A literature survey and internet screening revealed that nutraceuticals comprising a proper combination of natural edible seeds, herbs and medicinal plants has not yet been prepared to provide adequate nutrition and health protective benefits to the diabetics.

OBJECTS OF THE INVENTION

The main object of the present invention relates to the custom made tailored nutraceutical functional food composition(s), in a proper combination of natural edible seeds, herbs/medicinal plants to provide optimum nutrition, health protective, promotive and disease preventive benefits for diabetic patients.

Another object of the present invention is to provide an herbal health protective nutraceutical formulation, which obviates the drawbacks as detailed above.

Yet another object of the present invention is to formulate a combination of edible legumes, cereals, pseudocereals with promising potential for the development of base material to provide essential natural nutrients.

Still another object of the present invention is to develop health protective and disease preventive nutraceutical formulation, to ameliorate the general health of diabetics, as food supplements with specific functional attributes by fortifying nutritional base material with herbs/medicinal plants.

SUMMARY OF THE INVENTION

The present invention relates to the custom-made nutraceutical functional food composition(s), in a proper combination of natural edible seeds, herbs/medicinal plants to provide optimum nutrition, health protective, preventive and promotive benefits to ameliorate the general health of diabetics.

DETAILED DESCRIPTION

Accordingly, the present invention provides a herbal health protective, promotive and disease preventive nutraceutical composition(s) useful as food supplement to ameliorate the general health of people having diabetics with optimum nutrients and also help to control the blood sugar level, wherein the said formulation(s) comprising seed products selected from the group consisting of legumes, cereals and pseudocereals ranging from 50–90% by wt. and herbs/medicinal plants product ranging between 10–50% by wt.

Also, the present invention provide composition(s) used as herbal health protective, promotive nutraceutical formulation(s) for diabetics, said composition(s) comprising roasted seed powders, herbs/medicinal plants extract *Piper longum* (Pippali) fruits powder, *Curcuma longa* (Haldi) rhizomes powder, *Chlorophytum tuberosum* (Safed Musli) rhizomes powder and *Elettaria cardamomum* fruits powder.

The present invention also provide a process for the preparation of herbal health protective, promotive and disease preventive nutraceutical composition(s) useful as food supplement to ameliorate the general health of diabetics with optimum nutrients and also helps to control the blood sugar.

The process comprises the selected seeds of *Glycine max, Cicer arietinum, Phaseolus mungo, Cyamompsis tetragonoloba, Phaseolus radiatus, Mucuna pruriens, Hordeum vulgare, Amaranthus hypochondriacus* and *Fagopyrum esculantum* may be roasted by keeping in microwave oven (BPL-Sanyo, model BMO 800TS, frequency 2450 MHz) from 2 to 15 minutes, the roasted seeds 9 in numbers may be powdered separately to pass through a sieve ranging from 50 to 400 mesh, the seed powders may be mixed ranging from 0 to 90% by weight to get the base product(s), in a mixer grinder ranging from 5 to 60 minutes and may be called as base product(s), the roots, fruits, seeds, leaves, wood and whole plant of natural authentic herbs/medicinal plants may be selected from the group of *Gymnema sylvestre, Momordica charantia, Syzgium cumini, Pterocarpus marsupium, Trigonella foenum-graecum, Cinnamomum tamala, Withania somnifera, Coccinia indica, Pueraria tuberosa, Asparagus racemosus, Boerhaavia diffusa, Aegle marmelos, Piper longum, Curcuma longa, Chlorophytum tuberosum, Elettaria cardamomum*, may be cut into small pieces 1 to 15 cm, dried under shade at the temperature ranging from 20 to 50° C. and powdered ranging from 10 to 400 mesh, the powdered herbs/medicinal plants may be mixed ranging from 0 to 40% by wt. of the total mixture and may be extracted with aqueous alcohol in the range of 5 to 95% v/v thrice for 5 to 48 hours, at temperature ranging from 20 to 50° C., the alcohol may be selected from methanol, ethanol, propanol, isopropanol and butanol, the said solvent from combined extracts may be removed under reduced pressure ranging from 10 to 150 PSI at temperature ranging from 20 to 80° C. and the viscous residue thus obtained is called as plants extract, the residue may be suspended in ethanol-water mixture from 0 to 90% v/v in the ratio ranging from 10 to 30% by stirring for 5 to 60 minutes, the suspension of plants extract or plants powder may be mixed with roasted seeds powder mixture in the ratio ranging from 10 to 50% by wt., the mixture of plants extract or plants powder and roasted seed powders are mixed thoroughly in a mixer grinder for a period of ranging from 5 to 60 minutes, the mixture may be dried for a period of ranging from 5 to 50 hours at temperature ranging from 20 to 50° C., the amount of optional additives used may be in the range *piper longum* fruits powder 0.5 to 4% by wt, *Curcuma longa* rhizomes powder 0 to 4% by wt, *Chlorophytum tuberosum* rhizomes powder 0 to 4% by wt and *Elettaria cardamomum* fruits powder 0 to 4% by wt, the dried plants extract or plants powder and seeds powder mixture is again mixed thoroughly in a mixer grinder for a period of ranging from 5 to 60 minutes and the powder thus obtained is used to prepare final nutraceutical(s), the end product(s) is suitable for use in the form of powder, granules, biscuits, suspension, tablets or capsules etc for diabetics.

It was observed that the seeds selected from the group of *Glycine max, Cicer arietinum, Phaseolus mungo, Cyamompsis tetragonoloba* and *Hordeum vulgare* are essential, *Phaseolus radiatus, Mucuna pruriens, Amaranthus hypochondriacus* and *Fagopyrum esculantum* are optional. Among the herbs/medicinal plants selected from the group of *Gymnema sylvestre, Momordica charantia, Syzgium cumini, Pterocarpus marsupium, Trigonella foenum-graecum* and *Cinnamomum tamala*, are essential from the group comprising *Withania somnifera, Coccinia indica, Pueraria tuberosa, Asparagus racemosus, Boerhaavia diffusa* and *Aegle marmelos* are optional and selected from *Piper longum, Chlorophytum tuberosum, Curcuma longa* and *Elettaria cardamomum* are additional components of the value addition. The combination of the present nutraceutical(s) is not a mere admixture of the ingredients used resulting in aggregation of their properties but a mixture having synergistically enhanced properties useful as food supplement as health protective, promotive and disease preventive nutraceutical composition(s) to ameliorate the general health of diabetics with optimum nutrients and also help to control the blood sugar level.

In an embodiment of the invention to provide a herbal health protective, promotive and disease preventive nutraceutical herbal formulation(s) for diabetics and a process for preparing the same, wherein the said formulation(s) comprising seed products selected from the group consisting of legumes, cereals and pseudocereals ranging from 50–90% by wt. and herbs/medicinal plants product(s) ranging between 10–50% by wt.

In another embodiment of the invention, the seed products are selected from dried seeds, roasted seeds and powdered seeds.

In another embodiment of the invention, the legumes used is/are selected from the essential group comprising *Glycine max, Cicer arietinum, Phaseolus mungo* and *Cyamompsis tetragonoloba* and optionally selected from the group comprising, *Phaseolus radiatus* and *Mucuna pruriens*.

In still another embodiment of the invention, the total amount of legumes used is in the range from 30–80% by wt.

In another embodiment of the invention, the essential cereal used is *Hordeum vulgare*.

Yet another embodiment of the invention, the total amount of cereals used is in the range from 5–40% by wt.

In another embodiment of the invention, the pseudocereals used is/are selected from *Amaranthus hypochondriacus* and *Fagopyrum esculantum*.

Yet another embodiment of the invention, the total amount of pseudocereal used is in the range from 10–30% by wt.

Yet another embodiment of the invention, the essential herbs/medicinal plants used are selected from the group of *Gymnema sylvestre, Momordica charantia, Syzgium cumini, Pterocarpus marsupium, Trigonella foenum-graecum* and *Cinnamomum tamala*.

Yet another embodiment of the invention, the optional herbs/medicinal plants used are selected from the group comprising *Withania somnifera, Coccinia indica, Pueraria tuberosa, Asparagus racemosus, Boerhaavia diffusa* and *Aegle marmelos*.

Yet another embodiment of the invention, the said herbs/medicinal plant parts used are selected from roots, fruits, seeds, leaves, wood and whole plants.

Yet another embodiment of the invention, the total amount of herbs/medicinal plants used is X, wherein, X is in the range between 10 to 50% by wt of formulation(s).

Yet another embodiment of the invention, relates to the amount of the essential herbs/medicinal plants used are in the range between *Gymnema sylvestre* X (2–40% by wt.), *Momordica charantia* X (2–40% by wt.), *Syzgium cumini* X (2–40% by wt.), *Pterocarpus marsupium* X (2–40% by wt.), *Trigonella foenum-graecum* X (2–40% by wt.) and *Cinnamomum tamala* X (2–40% by wt.).

Yet another embodiment of the invention, the amount of the optional herbs/medicinal plants used are in the range between *Withania somnifera* X (0–20% by wt.), *Coccinia indica* X (0–20% by wt.), *Pueraria tuberosa* X (0–20% by wt.), *Asparagus racemosus* X (0–20% by wt.), *Boerhaavia diffusa* X (0–20% by wt.) and *Aegle marmelos* X (0–20% by wt.).

Yet another embodiment of the invention, the said herbal formulation optionally contain acceptable amounts of further additives selected from *Piper longum, Chlorophytum tuberosum, Curcuma longa* and *Elettaria cardamomum*.

One more embodiment of the invention relates to a herbal health protective, promotive and disease preventive nutraceutical(s) composition for diabetics, wherein the said formulation(s) consisting of seed powders mixture ranging from 50 to 90% by wt., herbs/medicinal plants powder or their extract ranging from 10 to 50% by wt. and the composition further comprising *Piper longum* fruits powder ranging from 0.5 to 4% by wt., *Curcuma longa* rhizomes powder ranging from 0 to 4% by wt., *Chlorophytum tubero-*

*sum* rhizomes powder ranging from 0 to 4% by wt. and *Elettaria cardamomum* fruits powder ranging from 0 to 4% by wt.

In yet another embodiment of the invention, the amount of legumes present in the composition(s) is in the range between 30–80% by wt., cereals in the range between 5–40% by wt. and psuedocereals in the range between 10–30% by wt. of the total seed powders mixture.

In yet another embodiment of the invention, the end-product(s) is suitable for use in the form of powder, granules, suspension, biscuits, tablets or capsules etc.

One more embodiment of the invention, relates to a process for the preparation of herbal health protective, promotive and preventive nutraceutical composition(s) useful as food supplements to ameliorate the general health of diabetics with optimum nutrients and also help to control the blood sugar level and disease related problems, the said process comprising:
a. selecting seed products from the group of *Glycine max, Cicer arietinum, Phaseolus mungo, P. radiatus, Cyamopsis tetragonoloba, Mucuna pruriens, Hordeum vulgare, Amaranthus hypochondriacus, Fagopyrum esculantum* and
b. roasting the seeds for 2 to 15 minutes under microwave conditions having frequency 1500–2500 MHz, powdering the roasted seeds to a mesh size of 50–400 and mixing the seed powders,
c. obtaining powder or extract of herbs/medicinal plants from the group of *Gymnema sylvestre, Momordica charantia, Syzgium cumini, Pterocarpus marsupium, Trigonella foenum-graecum, Cinnamomum tamala, Withania somnifera, Coccinia indica, Pueraria tuberosa, Asparagus racemosus, Boerhaavia diffusa* and *Aegle marmelos,*
d. and drying the extract to obtain a residue, mixing the plants extract residue with the base product to get the final nutraceutical product(s)
e. and optionally adding some additives selected from *piper longum, Curcuma longa, Chlorophytum tuberosum* and *Elettaria cardamomum* (Elaichi) fruits powder to obtain end nutraceutical product(s).

In another embodiment of the invention, the roasted seeds are powdered separately to pass through sieves having mesh size ranging from 50 to 400.

In another embodiment of the invention, the amount of roasted seed powders are mixed in various proportions ranging up to 40% by weight and parts of plants used are selected from roots, fruits, seeds, leaves, wood and whole plant of herbs/medicinal plants ranging up to 40% by wt. are selected for use in the nutraceutical product(s).

In yet another embodiment of the invention, the herbs/medicinal plants are cut into small pieces ranging from 1 to 15 cm, dried under shade at the temperature ranging from 20 to 50° C. and powdered ranging from 10 to 400 mesh.

In yet another embodiment of the invention, the crushed and powdered herbs/medicinal plants are mixed up to 40% by wt. of the total mixture.

In yet another embodiment of the invention, the powdered herbs/medicinal plants mixture is extracted with aqueous alcohol in the range of 5 to 95% v/v thrice for 5 to 48 hours, at temperature ranging from 20 to 50° C.

In yet another embodiment of the invention, the alcohol is selected from methanol, ethanol, propanol, isopropanol and butanol.

In yet another embodiment of the invention, the said solvent from combined extractives is removed under reduced pressure ranging from 10 to 150 PSI at temperature ranging from 20 to 80° C. and the viscous residue thus obtained is called as plants extract.

In yet another embodiment of the invention, the plants extract is suspended in ethanol-water mixture from 0 to 90% v/v in the ratio ranging from 10 to 30% by stirring for 5 to 60 minutes.

In yet another embodiment of the invention, the suspension of plants extract or plants powder is mixed with roasted seed powders mixture in the ratio ranging up to 50% by wt.

In yet another embodiment of the invention, the mixture of plants extract or plants powder and roasted seed powders are mixed thoroughly in a mixer grinder for a period of ranging from 5 to 60 minutes.

In yet another embodiment of the invention, the mixture is dried for a period of ranging from 5 to 50 hours at temperature ranging from 20 to 50° C.

In yet another embodiment of the invention, the amount of optional additives used are in the range *piper longum* fruits powder 0.5 to 4% by wt, *Curcuma longa* rhizomes powder 0 to 4% by wt, *Chlorophytum tuberosum* rhizomes powder 0 to 4% by wt and *Elettaria cardamomum* fruits powder 0 to 4% by wt.

In yet another embodiment of the invention, the dried plants extract or plants powder and seed powders mixture is again mixed thoroughly in a mixer grinder for a period of ranging from 5 to 60 minutes and the powder thus obtained is used to prepare final nutraceutical(s).

In yet another embodiment of the invention, the said dried plants extract or plants powder and seed powders mixture is mixed with in the ratio ranging up to 90% by wt.

In yet another embodiment of the invention, said mixture containing dried and powdered mixture of plants extract or powders thereof, roasted seed powders and *piper longum* fruits powder up to 4% by wt is added to the said mixture.

In yet another embodiment of the invention, *Curcuma longa* rhizomes powder up to 4% by wt is added to the said mixture.

In yet another embodiment of the invention, to the said mixture up to 4% by wt. *Elettaria cardamomum* seeds powder is added.

In yet another embodiment of the invention, powdered, mixture of plants extract or plants powder, roasted seed powders, *piper longum* fruits powder, *Curcuma longa* rhizomes powder, *Chlorophytum tuberosum* rhizomes powder and *Elettaria cardamomum* fruits powder mixture is mixed thoroughly in a mixer grinder for a period of ranging from 5 to 60 minutes to get the final nutraceutical product(s).

In yet another embodiment of the invention, the nutraceutical formulations, as herein described for the composition, methodology, preparation of base material for nutrition and fortified with selected herbs/medicinal plants in the form of powders/extracts to get the value added end nutraceutical product(s) which may be used as health protective, promotive, food supplements to ameliorate the general health of the diabetics and to control hyperglycemia in the form of powder, granules, biscuits, suspension, tablets or capsules etc.

Novelty:

The novelty of present invention is the specific combination of legumes, cereals, pseudocereals fortified with herbs/medicinal plants and the process for the preparation of nutraceuticals. The nutraceuticals are with optimum nutrition, non toxic, natural herbal plant products, easy to digest, have health protective and promotive properties to ameliorate the health and vigor of diabetics.

Besides controlling the blood/urine sugar level the nutraceutical product(s) provide additional benefits in diabetese related human health problems like reduction in fatigue, weakness, drowsiness, numbing effect, frequent urination, unusual thirst and hunger, weight loss, swellings on legs/ankles, burning sensation on feet, palms, relief in skin itching, skin dryness, black patches on skin, hypertension, increase in sleep comfort, energetic feeling, improvement in laziness, blurred vision, frequent skin infections and slow healing of wounds and sores. A 10–30% reduction in insulin doses was also observed after 6–8 weeks in IDDM adult diabetics and 30 to 100% reduction of oral medicines in NIDDM adult diabetics was found.

The present invention provides a process, without deteriorating the nutritional and pharmaceutical properties of the basic ingredients, for the preparation of custom-made herbal health protective nutraceutical(s) suitable as a nutraceutical food supplement for diebetics.

The present invention provides formulation(s) for the combination of edible legumes, cereals, pseudocereals with promising potential for the development of well balanced nutritional base material.

The present invention provides value added products with synergistic health promotive, protective and disease preventive effects of natural herbs/medicinal plants to get specifically designed nutraceutical(s) for well balanced natural nutrients, to get optimum nutrition to ameliorate the general health of diabetics.

BRIEF DESCRIPTION OF THE ACCOMPANYING TABLES

Table 1 provides the composition of the Nutraceutical formulation of the present invention and other commercial herbal antidiabetic products Tables 2 provides the percentage seed powders (legumes, cereals and pseudocereals) in the composition of the present invention.

Table 3 provides the percentage of herbs/medicinal plants in the composition of the present invention.

Table 4 provides the trial feed back remarks from volunteers on the nutraceutical product of the present invention.

Table 5 provides the trial feed back from volunteers after consuming the Herbal health protective and promotive Nutraceutical for diabetics for 3 months The invention is described with reference to the examples, which are provided by way of illustration only, and these examples should not be construed to limit the scope of the present invention.

EXAMPLES

Specific Combinations

To prepare nutraceutical formulation the seeds of *Glycine max, Cicer arietinum, Phaseolus mungo, Cyamopsis tetragonoloba, Mucuna pruriens, Hordeum vulgare, Amaranthus hypochondriacus* and *Fagopyrum esculantum* were roasted by keeping in microwave oven for 2 minutes separately. The microwave roasted seeds were powdered separately to pass through a 50-mesh sieve. The seed powders and herbs/medicinal plants extract were mixed as given in example 1.

Example 1

The microwave roasted seed powders of *Glycine max* 50 g, *Cicer arietinum* 100 g, *Phaseolus mungo* 50 g, *Cyamopsis tetragonoloba* 50 g, *Mucuna pruriens* 50 g, *Hordeum vulgare* 400 g, *Amaranthus hypochondriacus* 100 g and *Fagopyrum esculantum* 200 g were mixed for 20 minutes in a mixer grinder. The roots, fruits, bark, whole plant of natural authentic herbs/medicinal plants collected from different natural sources in India were cut into small pieces of about 1 cm, dried under shade at 20° C., crushed and powdered to 10-mesh. The dried powder of *Gymnema sylvestre* 20 g, *Momordica charantia* 50 g, *Syzgium cumini* 80 g, *Pterocarpus marsupium* 50 g, *Trigonella foenum-graecum* 100 g and *Cinnamomum tamala* 400 g, *Withania somnifera* 20 g, *Coccinia indica* 50 g, *Pueraria tuberosa* 200 g and *Boerhaavia diffusa* 30 g were extracted with 1.5 lit of aqueous alcohol 5% v/v thrice for 5 hours, at temperature 20° C., the solvent from combined extractives was removed under reduced pressure at 10 PSI, at temperature of 20° C. and the viscous residue thus obtained was called as the plants extract. The 10 g of plants extract was suspended in 20 ml water and mixed with mixer grinder for a period of 5 minutes, the suspension of plants extract was mixed with the 89.5 g mixture of roasted seed powders and mixed thoroughly for a period of 5 minutes. The plants extract and seed powders mixture was dried for 5 hours at 20° C. under vacuum, the dried plants extract and seed powders mixture was again mixed thoroughly in a mixer grinder for 5 minutes. The powder thus obtained was used to prepare final nutraceutical. The dried plants extract and seed powders mixture was mixed with the optional additives of *Piper longum* fruit powder 0.5 g and the total mixture was mixed thoroughly in a mixer grinder for 5 minutes to get the final nutraceutical product. The end product is suitable for use in the form of powder, granules, biscuits, suspension, tablets or capsules etc for diabetics.

Tables 2 provides the percentage seed powders (legumes, cereals and pseudocereals) in the composition of the present invention.

Table 3 provides the percentage of herbs/medicinal plants in the composition of the present invention.

The combination of the present nutraceutical is a mixture having synergistic (Table 4) health protective and promotive properties useful as food supplement to ameliorate the general health of diabetics with optimum nutrients and also help to control the blood sugar level (Table 5).

To prepare nutraceutical formulation the seeds of *Glycine max, Cicer arietinum, Phaseolus mungo, Cyamompsis tetragonoloba, Mucuna pruriens, Hordeum vulgare, Amaranthus hypochondriacus* and *Fagopyrum esculantum* were roasted by keeping in microwave oven for 12 minutes separately. The microwave-roasted seeds were powdered separately to pass through a 350-mesh sieve. The seed powders and herbs/medicinal plants extract were mixed as given in example 2.

Example 2

The microwave roasted seed powders of *Glycine max* 150 g, *Cicer arietinum* 100 g, *Phaseolus mungo* 50 g, *Cyamompsis tetragonoloba* 100 g, *Mucuna pruriens* 50 g, *Hordeum vulgare* 350 g, *Amaranthus hypochondriacus* 100 g and *Fagopyrum esculantum* 100 g were mixed in a mixer grinder for 55 minutes to get the base product. The roots, fruits, seeds, leaves, wood and whole plant of natural authentic herbs herbs/medicinal plants collected from different natural sources in India were cut into small pieces of about 12 cm, dried at 45° C., crushed and powdered to 350-mesh. The dried powder of *Gymnema sylvestre* 400 g, *Momordica charantia* 50 g, *Syzgium cumini* 20 g, *Pterocarpus marsupium* 100 g, *Trigonella foenum-graecum* 80 g, *Cinnamomum tamala* 50 g, *Withania somnifera* 30 g, *Asparagus racemosus* 200 g, *Boerhaavia difussa* 20 g and *Aegle marmelos* 50 g were extracted with 1.75 lit ml aqueous alcohol 80% v/v thrice for 42 hours, at 45° C., the solvent from combined extractives was removed under reduced pressure at 125 PSI at temperature 70° C. and the viscous residue thus obtained is called as plants extract. The 20 g plants extract was suspended in 60 ml of 80% water-ethanol mixture by stirring for 50 minutes, the suspension of plants extract was mixed with 75 g of roasted seeds powder mixture and mixed thoroughly in a mixer grinder for a period of 55 minutes. The mixture was dried for a period of 45 hours at temperature 50° C. The powder thus obtained was used to prepare final nutraceutical. The dried plants extract and seed powders mixture was mixed with the optional additives of *Piper longum* fruits powder 1.0 g, *Curcuma longa* rhizomes powder 1.5 g, *Chlorophytum tuberosum* rhizomes powder 2.0 g and *Elettaria cardamomum* fruits powder 0.5 g the total mixture was again mixed thoroughly in a mixer grinder for a period of 55 minutes to get the final nutraceutical. The end product is suitable for use in the form of powder, granules, biscuits, suspension, tablets or capsules etc for diabetics.

The combination of the present nutraceutical is a mixture having synergistic (Table 4) health protective and promotive properties useful as food supplement to ameliorate the general health of diabetics with optimum nutrients and also help to control the blood sugar (Table 5).

To prepare nutraceutical formulation the seeds of *Glycine max, Cicer arietinum, Phaseolus mungo, Cyamompsis tetragonoloba, Mucuna pruriens, Hordeum vulgare, Amaranthus hypochondriacus* and *Fagopyrum esculantum* were roasted by keeping in microwave oven for 10 minutes separately. The microwave roasted seeds were powdered separately to pass through a 300-mesh sieve. The seed powders and herbs/medicinal plants extract were mixed as given in example 3.

Example 3

The microwave roasted seeds, were powdered of *Glycine max* 150 g, *Cicer arietinum* 150 g, *Phaseolus mungo* 100 g, *Cyamompsis tetragonoloba* 50 g, *Mucuna pruriens* 50 g, *Hordeum vulgare* 300 g, *Amaranthus hypochondriacus* 150 g and *Fagopyrum esculantum* 50 g were mixed in a mixer grinder for 50 minutes to get the base product. The roots, fruits, seeds, leaves, wood and whole plant of natural authentic herbs herbs/medicinal plants collected from different natural sources in India were cut into small pieces of about 10 cm, dried at 40° C., crushed and powdered to 300-mesh. The dried powder of *Gymnema sylvestre* 20 g, *Momordica charantia* 80 g, *Syzgium cumini* 100 g, *Pterocarpus marsupium* 150 g, *Trigonella foenum-graecum* 150 g, *Cinnamomum tamala* 200 g, *Withania somnifera* 50 g, *Coccinia indica* 200 g, *Pueraria tuberosa* 30 g and *Asparagus racemosus* 20 g were extracted with 1.7 ml aqueous alcohol 70% v/v thrice for 40 hours, at 40° C., the solvent from combined extractives was removed under reduced pressure at 100 PSI at temperature 60° C. and the viscous residue thus obtained is called as plants extract. The 25 g plants extract was suspended in 75 ml of 70% water-ethanol mixture by stirring for 45 minutes, the suspension of plants extract was mixed with 70 g of roasted seeds powder mixture and mixed thoroughly in a mixer grinder for a period of 50 minutes. The mixture was dried for a period of 40 hours at temperature 45° C. The powder thus obtained was used to prepare final nutraceutical. The dried plants extract and seed powders mixture was mixed with the optional additives of *Piper longum* fruits powder 1.0 g and *Elettaria cardamomum* fruits powder 4.0 g, and the total mixture was again mixed thoroughly in a mixer grinder for a period of 45 minutes to get the final nutraceutical. The end product is suitable for use in the form of powder, granules, biscuits, suspension, tablets or capsules etc for diabetics.

The combination of the present nutraceuticals is a mixture having synergistic (Table 4) health protective and promotive properties useful as food supplement to ameliorate the general health of diabetics with optimum nutrients and also help to control the blood sugar (Table 5).

To prepare nutraceutical formulation the seeds of *Glycine max, Cicer arietinum, Phaseolus mungo, Cyamompsis tetragonoloba, Phaseolus raditus, Hordeum vulgare, Amaranthus hypochondriacus* and *Fagopyrum esculantum* were roasted by keeping in microwave oven for 8 minutes separately. The microwave roasted seeds were powdered separately to pass through a 250-mesh sieve. The seed powders and herbs/medicinal plants extract were mixed as given in example 4.

Example 4

The microwave roasted seeds, were powdered of *Glycine max* 200 g, *Cicer arietinum* 150 g, *Phaseolus mungo* 100 g, *Cyamompsis tetragonoloba* 50 g, *Phaseolus raditus* 50 g, *Hordeum vulgare* 250 g, *Amaranthus hypochondriacus* 150 g and *Fagopyrum esculantum* 50 g were mixed in a mixer grinder for 45 minutes to get the base product. The roots, fruits, seeds, leaves, wood and whole plant of natural authentic herbs herbs/medicinal plants collected from different natural sources in India were cut into small pieces of about 8.0 cm, dried at 35° C., crushed and powdered to 200-mesh. The dried powder of *Gymnema sylvestre* 100 g, *Momordica charantia* 20 g, *Syzgium cumini* 80 g, *Pterocarpus marsupium* 150 g, *Trigonella foenum-graecum* 200 g, *Cinnamomum tamala* 150 g, *Withania somnifera* 200 g, *Coccinia indica* 20 g, *Pueraria tuberosa* 50 g and *Asparagus racemosus* 30 g were extracted with 1.6 lit aqueous alcohol 60% v/v thrice for 35 hours, at 38° C., the solvent from combined extractives was removed under reduced pressure at 90 PSI at temperature 55° C. and the viscous residue thus obtained is called as plants extract. The 30 g plants extract was suspended in 90 ml of 60% water-ethanol mixture by stirring for 40 minutes, the suspension of plants extract was mixed with 65 g of roasted seeds powder mixture and mixed thoroughly in a mixer grinder for a period of 45 minutes. The mixture was dried for a period of 35 hours at temperature 40° C. The powder thus obtained was used to prepare final nutraceutical. The dried plants extract and seed powders mixture was mixed with the optional additives of *Piper longum* fruits powder 1.0 g and *Chlorophytum tuberosum* rhizomes powder 4.0 g, the total mixture was again mixed thoroughly in a mixer grinder for a period of 40 minutes to get the final nutraceutical. The end product is suitable for use in the form of powder, granules, biscuits, suspension, tablets or capsules etc for diabetics.

The combination of the present nutraceuticals is a mixture having synergistic (Table 4) health protective and promotive properties useful as food supplement to ameliorate the general health of diabetics with optimum nutrients and also help to control the blood sugar (Table 5).

To prepare nutraceutical formulation the seeds of *Glycine max, Cicer arietinum, Phaseolus mungo, Cyamompsis tetragonoloba, Phaseolus raditus, Mucuna pruriens, Hordeum vulgare, Amaranthus hypochondriacus* and *Fagopyrum esculantum* were roasted by keeping in microwave oven for 6 minutes separately. The microwave roasted seeds were powdered separately to pass through a 200-mesh sieve. The seed powders and herbs/medicinal plants extract were mixed as given in example 5.

Example 5

The microwave roasted seeds, were powdered of *Glycine max* 200 g, *Cicer arietinum* 100 g, *Phaseolus mungo* 50 g, *Cyamompsis tetragonoloba* 50 g, *Phaseolus raditus* 100 g, *Mucuna pruriens* 100 g, *Hordeum vulgare* 150 g, *Amaranthus hypochondriacus* 200 g and *Fagopyrum esculantum* 50 g were mixed in a mixer grinder for 40 minutes to get the base product. The roots, fruits, seeds, leaves, wood and whole plant of natural authentic herbs herbs/medicinal plants collected from different natural sources in India were cut into small pieces of about 6.0 cm, dried at 30° C., crushed and powdered to 150-mesh. The dried powder of *Gymnema sylvestre* 50 g, *Momordica charantia* 50 g, *Syzgium cumini* 20 g, *Pterocarpus marsupium* 80 g, *Trigonella foenum-graecum* 400 g, *Cinnamomum tamala* 100 g, *Coccinia indica* 30 g, *Asparagus racemosus* 30 g, *Boerhaavia difussa* 200 g and *Aegle marmelos* 20 g were extracted with 1.5 lit aqueous alcohol 50% v/v thrice for 30 hours, at 35° C., the solvent from combined extractives was removed under reduced pressure at 80 PSI at temperature 50° C. and the viscous residue thus obtained is called as plants extract. The 35 g plants extract was suspended in 130 ml of 50% water-ethanol mixture by stirring for 35 minutes, the suspension of plants extract was mixed with 60 g of roasted seeds powder mixture and mixed thoroughly in a mixer grinder for a period of 40 minutes. The mixture was dried for a period of 30 hours at temperature 40° C. The powder thus obtained was used to prepare final nutraceutical. The dried plants extract and seed powders mixture was mixed with the optional additives of *Piper longum* fruits powder 4.0 g and *Curcuma longa* rhizomes powder 1.0 g, the total mixture was again mixed thoroughly in a mixer grinder for a period of 35 minutes to get the final nutraceutical. The end product is suitable for use in the form of powder, granules, biscuits, suspension, tablets or capsules etc for diabetics.

The combination of the present nutraceuticals is a mixture having synergistic (Table 4) health protective and promotive properties useful as food supplement to ameliorate the general health of diabetics with optimum nutrients and also help to control the blood sugar (Table 5).

To prepare nutraceutical formulation the seeds of *Glycine max, Cicer arietinum, Phaseolus mungo, Cyamompsis tetragonoloba, Phaseolus raditus, Hordeum vulgare* and *Amaranthus hypochondriacus* were roasted by keeping in microwave oven for 5 minutes separately. The microwave roasted seeds were powdered separately to pass through a 150-mesh sieve. The seed powders and herbs/medicinal plants extract were mixed as given in example 6.

Example 6

The microwave roasted seeds, were powdered of *Glycine max* 100 g, *Cicer arietinum* 400 g, *Phaseolus mungo* 30 g, *Cyamompsis tetragonoloba* 20 g, *Phaseolus raditus* 150 g, *Hordeum vulgare* 150 g and *Amaranthus hypochondriacus* 100 g were mixed in a mixer grinder for 30 minutes to get the base product. The roots, fruits, seeds, leaves, wood and whole plant of natural authentic herbs herbs/medicinal plants collected from different natural sources in India were cut into small pieces of about 5.0 cm, dried at 30° C., crushed and powdered to 100-mesh. The dried powder of *Gymnema sylvestre* 80 g, *Momordica charantia* 100 g, *Syzgium cumini* 50 g, *Pterocarpus marsupium* 400 g, *Trigonella foenum-graecum* 50 g, *Cinnamomum tamala* 20 g, *Withania somnifera* 10 g, *Coccinia indica* 20 g, *Pueraria tuberosa* 20 g, *Boerhaavia difussa* 50 g and *Aegle marmelos* 200 g were extracted with 1.25 lit aqueous alcohol 40% v/v thrice for 25 hours, at 30° C., the solvent from combined extractives was removed under reduced pressure at 70 PSI at temperature 45° C. and the viscous residue thus obtained is called as plants extract. The 40 g plants extract was suspended in 160 ml of 50% water-ethanol mixture by stirring for 35 minutes, the suspension of plants extract was mixed with 55 g of roasted seeds powder mixture and mixed thoroughly in a mixer grinder for a period of 35 minutes. The mixture was dried for a period of 25 hours at temperature 35° C. The powder thus obtained was used to prepare final nutraceutical. The dried plants extract and seed powders mixture was mixed with the optional additives of *Piper longum* fruits powder 3.0 g, *Chlorophytum tuberosum* rhizomes powder 1.5 g and *Elettaria cardamomum* fruits powder 0.5 g, and the total mixture was again mixed thoroughly in a mixer grinder for a period of 30 minutes to get the final nutraceutical. The end product is suitable for use in the form of powder, granules, biscuits, suspension, tablets or capsules etc for diabetics.

The combination of the present nutraceuticals is a mixture having synergistic (Table 4) health protective and promotive properties useful as food supplement to ameliorate the general health of diabetics with optimum nutrients and also help to control the blood sugar (Table 5).

To prepare nutraceutical formulation the seeds of *Glycine max, Cicer arietinum, Phaseolus mungo, Cyamompsis tetragonoloba, Hordeum vulgare* and *Fagopyrum esculantum* were roasted by keeping in microwave oven for 5 minutes separately. The microwave roasted seeds were powdered separately to pass through a 150-mesh sieve. The seed powders and herbs/medicinal plants extract were mixed as given in example 7.

Example 7

The microwave roasted seeds, were powdered of *Glycine max* 250 g, *Cicer arietinum* 200 g, *Phaseolus mungo* 150 g, *Cyamompsis tetragonoloba* 150 g, *Hordeum vulgare* 100 g and *Fagopyrum esculantum* 200 g were mixed in a mixer grinder for 20 minutes to get the base product. The roots, fruits, seeds, leaves, wood and whole plant of natural authentic herbs herbs/medicinal plants collected from different natural sources in India were cut into small pieces of about 3.0 cm, dried at 25° C., crushed and powdered to 60-mesh. The dried powder of *Gymnema sylvestre* 100 g, *Momordica charantia* 50 g, *Syzgium cumini* 400 g, *Pterocarpus marsupium* 20 g, *Trigonella foenum-graecum* 80 g, *Cinnamomum tamala* 50 g, *Withania somnifera* 100 g, *Coccinia indica* 100 g and *Boerhaavia difussa* 100 g were extracted with 1.2 lit aqueous alcohol 30% v/v thrice for 20 hours, at 30° C., the solvent from combined extractives was removed under reduced pressure at 60 PSI at temperature 40° C. and the viscous residue thus obtained is called as plants extract. The 45 g plants extract was suspended in 230 ml of 40% water-ethanol mixture by stirring for 25 minutes, the suspension of plants extract was mixed with 50 g of roasted seeds powder mixture and mixed thoroughly in a mixer grinder for a period of 30 minutes. The mixture was dried for a period of 20 hours at temperature 30° C. The powder thus obtained was used to prepare final nutraceuticals. The dried plants extract and seed powders mixture was mixed with the optional additives of *Piper longum* fruits powder 1.0 g and *Curcuma longa* rhizomes powder 4.0 g and the total mixture was again mixed thoroughly in a mixer grinder for a period of 20 minutes to get the final nutraceutical. The end product is suitable for use in the form of powder, granules, biscuits, suspension, tablets or capsules etc for diabetics.

The combination of the present nutraceuticals is a mixture having synergistic (Table 4) health protective and promotive properties useful as food supplement to ameliorate the general health of diabetics with optimum nutrients and also help to control the blood sugar (Table 5).

To prepare nutraceutical formulation the seeds of *Glycine max, Cicer arietinum, Phaseolus mungo, Cyamompsis tetragonoloba, Hordeum vulgare, Amaranthus hypochondriacus* and *Fagopyrum esculantum* were roasted by keeping in microwave oven for 15 minutes separately. The microwave roasted seeds were powdered separately to pass through a 400-mesh sieve. The seed powders and herbs/medicinal plants extract were mixed as given in example 8.

Example 8

The microwave roasted seeds, were powdered of *Glycine max* 300 g, *Cicer arietinum* 100 g, *Phaseolus mungo* 200 g, *Cyamompsis tetragonoloba* 200 g, *Hordeum vulgare* 50 g, *Amaranthus hypochondriacus* 50 g and *Fagopyrum esculantum* 150 g were mixed in a mixer grinder for 60 minutes to get the base product. The roots, fruits, seeds, leaves, wood and whole plant of natural authentic herbs herbs/medicinal plants collected from different natural sources in India were cut into small pieces of about 15 cm, dried at 50° C., crushed and powdered to 400-mesh. The dried powder of *Gymnema sylvestre* 50 g, *Momordica charantia* 400 g, *Syzgium cumini* 100 g, *Pterocarpus marsupium* 50 g, *Trigonella foenum-graecum* 20 g, *Cinnamomum tamala* 80 g, *Pueraria tuberosa* 100 g, *Asparagus racemosus* 100 g and *Aegle marmelos* 100 g were extracted with 2.0 lit aqueous alcohol 90% v/v thrice for 48 hours, at 50° C., the said solvent from combined extractives was removed under reduced pressure at 150 PSI at temperature 80° C. and the viscous residue thus obtained is called as plants extract. The 49.5 g plants extract was suspended in 300 ml of 90% water-ethanol mixture by stirring for 60 minutes, the suspension of plants extract was mixed with 50 g of roasted seeds powder mixture and mixed thoroughly in a mixer grinder for a period of 60 minutes. The mixture was dried for a period of 50 hours at temperature 50° C. The powder thus obtained was used to prepare final nutraceutical. The dried plants extract and seed powders mixture was mixed with the optional additives of *Piper longum* fruits powder 0.5 g and the total mixture was again mixed thoroughly in a mixer grinder for a period of 60 minutes to get the final nutraceutical. The end product is suitable for use in the form of powder, granules, biscuits, suspension, tablets or capsules etc for diabetics.

The combination of the present nutraceutical(s) is a mixture having synergistic (Table 4) health protective and promotive properties useful as food supplement to ameliorate the general health of diabetics with optimum nutrients and also help to control the blood sugar (Table 5).

Advantages

Include control in blood/urine sugar levels, ameliorate diabetes related health problems like reduction in fatigue, weakness, drowsiness, numbing effect, frequent urination, unusual thirst and hunger, weight loss, swellings on legs/ankles, burning sensation on feet, palms, relief in skin itching, skin dryness, black patches on skin, hypertension, increase in sleep comfort, feeling more energetic, improvement in laziness, blurred vision, frequent skin infections and slow healing of wounds and sores. A 10–30% reduction in insulin doses was also observed after 6–8 weeks in IDDM adult diabetics and 30 to 100% reduction of oral medicines in NIDDM adult diabetics was found.

TABLE 1

The composition of the present nutraceutical formulation(s) (Nutra-Diab) and commercial herbal antidiabetic products.

| Nutraceutical formulation(s) | Commercial herbal antidiabetic products |
|---|---|
| Example 1: Glycine max 4.475, Cicer arietinum 8.95, Phaseolus mungo 4.475, Cyamompsis tetragonoloba 4.475, Mucuna pruriens 4.475, Hordeum vulgare 35.8, Amaranthus hypochondriacus 8.95, Fagopyrum esculantum 17.9, Gymnema sylvestre 0.2, Momordica charantia 0.5, Syzgium cumini 0.8, Pterocarpus marsupium 0.5, Trigonella foenum-graecum 1.0, Cinnamomum tamala 4.0, Withania somnifera 0.2, Coccinia indica 0.5, Pueraria tuberosa 2.0, Boerhaavia difussa 0.4 and Piper longum 0.5% by wt.. | Cogent-db: Each tablet is prepared out of Azadirecta indica bark 3 g, Phyllanthus emblica 0.7 g, Terminalia bellerica 0.7 g, T. chebula 0.7 g, Tribulus terrestris 1.0 g, Aconitum heterophyllum 0.1 g, Curcuma longa 0.8 g, Syzygium cumini 2.0 g, Rotula aquatica 1.0 g. |
| Example 2: Glycine max 11.25, Cicer arietinum 7.5, Phaseolus mungo 3.75, Cyamompsis tetragonoloba 7.5, Mucuna pruriens 3.75, Hordeum vulgare 26.25, Amaranthus hypochondriacus 7.5, Fagopyrum esculantum 7.5, Gymnema sylvestre 8.0, Momordica charantia 1.0, Syzgium cumini 0.4, Pterocarpus marsupium 2.0, Trigonella foenum-graecum 1.6, Cinnamomum tamala 1.0, Withania somnifera 0.6, Asparagus racemosus 4.0, Boerhaavia difussa 0.4, | Diabyog Capsules: Each capsule of 500 mg contain Basant Kusumakar Ras 60 mg, Yasad Bhasam 5 mg, Vang Bhasam 5 mg, Raj Jambu Beej 100 mg, Guduchi 40 mg, Sudh Shilajeet 30 mg, Meshasringi 60 mg, Shushavi Ghan 50 mg, Neem Ghan 30 mg, Methi Ghan 30 mg, Vijayasaar 50 mg, Goshul 20 mg, Punamava 20 mg. |

TABLE 1-continued

*Aegle marmelos* 1.0, *Piper longum* 1.0, *Curcuma longa* 1.5, *Chlorophytum tuberosum* 2.0 and *Elettaria cardamomum* 0.5% by wt..

Example 3: *Glycine max* 10.5, *Cicer arietinum* 10.5, *Phaseolus mungo* 7.0, *Cyamompsis tetragonoloba* 3.5, *Mucuna pruriens* 3.5, *Hordeum vulgare* 21.0, *Amaranthus hypochondriacus* 10.5 *Fagopyrum esculantum* 3.5, *Gymnema sylvestre* 0.5, *Momordica charantia* 2.0, *Syzgium cumini* 2.5, *Pterocarpus marsupium* 3.75, *Trigonella foenum-graecum* 3.75, *Cinnamomum tamala* 5.0, *Withania somnifera* 1.25, *Coccinia indica* 5.0, *Pueraria tuberosa* 0.75, *Asparagus racemosus* 0.5, *Piper longum* 1.0 and *Elettaria cardamomuin* 4.0%.

Example 4: *Glycine max* 13.0, *Cicer arietinum* 9.75, *Phaseolus mungo* 6.5, *Cyamompsis tetragonoloba* 3.25, *Phaseolus raditus* 3.25, *Hordeum vulgare* 16.25, *Amaranthus hypochondriacus* 9.75, *Fagopyrum esculantum* 3.25, *Gymnema sylvestre* 3.0, *Momordica charantia* 0.6, *Syzgium cumini* 2.4, *Pterocarpus marsupium* 4.5, *Trigonella foenum-graecum* 6.0, *Cinnamomum tamala* 4.5, *Withania somnifera* 6.0, *Coccinia indica* 0.6, *Pueraria tuberosa* 1.5, *Asparagus racemosus* 0.9, *Piper longum* 1.0 and *Chlorophytum tuberosum* 4.0%.

Example 5: *Glycine max* 12.0, *Cicer arietinum* 6.0, *Phaseolus mungo* 3.0, *Cyamompsis tetragonoloba* 3.0, *Phaseolus raditus* 6.0, *Mucuna pruriens* 6.0, *Hordeum vulgare* 9.0, *Amaranthus hypochondriacus* 12.0, *Fagopyrum esculantum* 3.0, *Gymnema sylvestre* 1.75, *Momordica charantia* 1.75, *Syzgium cumini* 0.7, *Pterocarpus marsupium* 2.8, *Trigonella foenum-graecum* 14.0, *Cinnamomum tamala* 3.5, *Coccinia indica* 1.05, *Asparagus racemosus* 1.75, *Boerhaavia difussa* 7.0, *Aegle marmelos* 0.7, *Piper longum* 4.0 and *Curcuma longa* 1.0%.

Example 6: *Glycine max* 5.5, *Cicer arietinum* 22.0, *Phaseolus mungo* 1.65, *Cyamompsis tetragonoloba* 1.1, *Phaseolus raditus* 8.2, *Hordeum vulgare* 11.0, *Amaranthus hypochondriacus* 5.5, *Gymnema sylvestre* 3.2, *Momordica charantia* 4.0, *Syzgium cumini* 2.0, *Pterocarpus marsupium* 16.0, *Trigonella foenum-graecum* 2.0, *Cinnamomum tamala* 0.8, *Withania somnifera* 0.4, *Coccinia indica* 0.8, *Pueraria tuberosa* 0.8, *Boerhaavia difussa* 2.0, *Aegle marmelos* 8.0, *Piper longum* 3.0, *Chlorophytum tuberosum* 1.5 and *Elettaria cardamomum* 0.5%.

Example 7: *Glycine max* 12.5, *Cicer arietinum* 10.0, *Phaseolus mungo* 7.5, *Cyamompsis tetragonoloba* 7.5, *Hordeum vulgare* 5.0, *Fagopyrum esculantum* 7.5, *Gymnema sylvestre* 4.5, *Momordica charantia* 2.25, *Syzgium cumini* 18.0, *Pterocarpus marsupium* 0.9, *Trigonella foenum-graecum* 3.6, *Cinnamomum tamala* 2.25, *Withania somnifera* 4.5, *Coccinia indica* 4.5, *Boerhaavia difussa* 4.5, *Piper longum* 1.0 and *Curcuma longa* 4.0%.

Example 8: *Glycine max* 15.0, *Cicer arietinum* 5.0, *Phaseolus mungo* 10.0, *Cyamompsis tetragonoloba* 10.0, *Hordeum vulgare* 2.5, *Amaranthus hypochondriacus* 2.5, *Fagopyrum esculantum* 5.0, *Gymnema sylvestre* 2.475, *Momordica charantia* 19.8, *Syzgium cumini* 4.95, *Pterocarpus marsupium* 2.475, Diabyog Granules: Each gram contain Swarn Makshik Bhasam 20 mg, Trivang Bhasam 20 mg, Shilajeet Shudh 60 mg, Meshasringi 60 mg, Shushavi Ghan 50 mg, Raj Jambu Beej 100 mg, Guduchi, Arjun, Gokshus, Neem, Bhumlamlabi, Raj Jambu Patra, Methini, Safed Chandan, Punarnava, Satavar each 50 mg/g, Twak 30 mg, Vijayasaar, Kramuka, Aguru each 3.3 mg, Excepient Q.S.

Diabecon: Extract Meshashringi 30 mg, Pitasara 20 mg, Yashti-madhu 20 mg, Saptarangi 20 mg, Jambu 20 mg, Shatavari 20 mg, Punarnava 20 mg, Mundatika 10 mg, Guduchi 10 mg, Kairata 10 mg, Gokshura 10 mg, Bhumyaamlaki 10 mg, Gumbhari 10 mg, Karpasi 10 mg, Karpasi 10 mg, Daruharidra 5 mg, Kumari 5 mg, Triphala 3 mg, Pdrs. Guggule (purified) 30 mg, Shilajeet (purified) 30 mg, Vidangadi lauham 27 mg, Sushavi 20 mg, Maricha 10 mg, Vishnu priya 10 mg, Atibala 10 mg, Haridra 10 mg, Abhrak bhasam 10 mg, Praval bhasam 10 mg, Jungli palak 5 mg, Vang bhasam 5 mg, Akik pisti 5 mg, Shingraf 5 mg, Yasad bhasam 5 mg, Trikuta 5 mg. Processed in Udumbara, Babbula puga, Ashvagandha, Tagara, Shyonaka, Chandana, Sunthi, Jambu.

Madhu Mehari Granules: *Gymnema sylsylvestra* 10%, *Syzygium cumini* 10%, *Memordica charantia* 10%, *Tinosphora cordifolia* 10%, *Acacia catechu* 5%, *Emblica officinalis* 10%, *Pterocarpus marsupium* 5%, *Ficus racemosa* 5%, *Picrorhiza kurroa* 5%, *Trigonella foenum-graecum* 5%, *Asphaltum punjabinum* 10%, Trivang Bhasm 2%, Abhrak Bhasm 2%, Swarn Makshik Bhasm 2%, Excepient starch-lactose 4% w/w.

Madhu Sunya: Each Kg contain Gudmar Fali 150 g, Jamun Seed 150 g, Karela Seed, 100 g, Kundru Root 100 g, Asgandha 100 g, Pure Shilajeet 10 g, Gurhal Pushp 50 g, Tulsi Root 90 g, Vijayasaar Wood 150 g.

Madhumeh Amrit: *Azadirecta indica* (leaves) 10, *Aegle marmelos* (leaves) 10, *Gymnema sylvestra* 10, *Syzygium cumini* (seeds) 10, *Ficus glomerata* (fruits) 10, *Sphaeranthus indicus* 10, *Leucas cephalotus* 10, *Trigonella foenum-graecum* 5.0, *Symplocos racemosus* 2.0, *Piper cubeb* 2.0, *Nyctanthes arbortristis* (flowers) 1.0, *Withania somnifera* 3.0, *Mucuna prurita* 3.0, Shilajit 1.0, *Phyllanthus emblica* 2.0, *Terminalia chebula* 1.0, *Terminalia belerica* 1.0, *Aegle marmelos* 1.0, *Memordica charantia* (seeds) 3.0, *Zingiber officinale* 5.0%.

TABLE 1-continued

*Trigonella foenum-graecum* 0.99, *Cinnamomum tamala* 3.96, *Pueraria tuberosa* 4.95, *Asparagus racemosus* 4.95, *Aegle marmelos* 4.95 and *Piper longum* 0.5%.

The amount of (% composition) of herbs/medicinal plants extract, seed powders and additional additives in the end nutraceutical products (Nutra-diab).

| Examples | 1 | 2 | 3 | 4 | 5 | 6 | 7 | 8 |
|---|---|---|---|---|---|---|---|---|
| Plants extract % | 10 | 20 | 25 | 30 | 35 | 40 | 45 | 49.5 |
| Seed powders % | 89.5 | 75 | 70 | 65 | 60 | 55 | 50 | 50 |
| Additives % | 0.5 | 5 | 5 | 5 | 5 | 5 | 5 | 0.5 |

TABLE 2

The amount of (% composition) of seed powders (legumes, cereals & pseudocereals) in the base products. (Nutra-Diab)

| | Example Nos | | | | | | | | |
|---|---|---|---|---|---|---|---|---|---|
| | 1 | 2 | 3 | 4 | 5 | 6 | 7 | 8 | % Range |
| Essential Legumes | | | | | | | | | |
| *Glycine max* | 5 | 15 | 15 | 20 | 20 | 10 | 25 | 30 | 5–30% |
| *Cicer arietinum* | 10 | 10 | 15 | 15 | 10 | 40 | 20 | 10 | 10–40% |
| *Phaseolus mungo* | 5 | 5 | 10 | 10 | 5 | 3 | 15 | 20 | 3–20% |
| *Cyamopsis tetragonoloba* | 5 | 10 | 5 | 5 | 5 | 2 | 15 | 20 | 2–20% |
| Optional Legumes | | | | | | | | | |
| *Phaseolus radiatus* | 0 | 0 | 0 | 5 | 10 | 15 | 0 | 0 | 0–15% |
| *Mucuna pruriens* | 5 | 5 | 5 | 0 | 10 | 0 | 0 | 0 | 0–10% |
| Total Legumes* | 30 | 45 | 50 | 55 | 60 | 70 | 75 | 80 | 30–80% |
| Cereal (Essential) | | | | | | | | | |
| *Hordeum vulgare* | 40 | 35 | 30 | 25 | 15 | 20 | 10 | 5 | 5–40% |
| Total cereals** | 40 | 35 | 30 | 25 | 15 | 20 | 10 | 5 | 5–40% |
| Pseudo Cereals (Optional) | | | | | | | | | |
| *A. hypochondriacus* | 10 | 10 | 15 | 15 | 20 | 10 | 0 | 5 | 0–20% |
| *Fagopyrum esculantum* | 20 | 10 | 5 | 5 | 5 | 0 | 15 | 10 | 0–20% |
| Total pseudo Cereals*** | 30 | 20 | 20 | 20 | 25 | 10 | 15 | 15 | 10–30% |

SUMMARY of the % Composition of seed powders in base product (Table 1)

| | Example Nos | | | | | | | | |
|---|---|---|---|---|---|---|---|---|---|
| Ingredients % | 1 | 2 | 3 | 4 | 5 | 6 | 7 | 8 | % Range |
| *Total Legumes | 30 | 45 | 50 | 55 | 60 | 70 | 75 | 80 | 30–80% |
| **Total Cereals | 40 | 35 | 30 | 25 | 15 | 20 | 10 | 5 | 5–40% |
| ***Total Pseudocereals | 30 | 20 | 20 | 20 | 25 | 10 | 15 | 15 | 10–30% |

TABLE 3

The amount of (% composition) of herbs/medicinal plants in the total mixture used for extraction/or as powder.

| | Example Nos | | | | | | | | |
|---|---|---|---|---|---|---|---|---|---|
| Herbs/medicinal plants | 1 | 2 | 3 | 4 | 5 | 6 | 7 | 8 | % Range |
| Essential | | | | | | | | | |
| *Gymnema sylvestre* | 2 | 40 | 2 | 10 | 5 | 8 | 10 | 5 | 2–40% |
| *Momordica charantia* | 5 | 5 | 8 | 2 | 5 | 10 | 5 | 40 | 2–40% |
| *Syzgium cumini* | 8 | 2 | 10 | 8 | 2 | 5 | 40 | 10 | 2–40% |
| *Pterocarpus marsupium* | 5 | 10 | 15 | 15 | 8 | 40 | 2 | 5 | 2–40% |
| *Trigonella foenum-graecum* | 10 | 8 | 15 | 20 | 40 | 5 | 8 | 2 | 2–40% |
| *Cinnamomum tamala* | 40 | 5 | 20 | 15 | 10 | 2 | 5 | 8 | 2–40% |
| Optional Herbs | | | | | | | | | |
| *Withania somnifera* | 2 | 3 | 5 | 20 | 0 | 1 | 10 | 0 | 0–20% |
| *Coccinia indica* | 5 | 0 | 20 | 2 | 3 | 2 | 10 | 0 | 0–20% |
| *Pueraria tuberosa* | 20 | 0 | 3 | 5 | 0 | 2 | 0 | 10 | 0–20% |
| *Asparagus recemosus* | 0 | 20 | 2 | 3 | 5 | 0 | 0 | 10 | 0–20% |
| *Boerhaavia diffusa* | 3 | 2 | 0 | 0 | 20 | 5 | 10 | 0 | 0–20% |
| *Aegle marmelos* | 0 | 5 | 0 | 0 | 2 | 20 | 0 | 10 | 0–20% |

Additional Herbs: *Piper longum*, *Curcuma longa*, *Chlorophytum tuberosum* and *Elettaria cardamomum* were used in the range of up to 4.0% in the end product(s).

TABLE 4

Trial feed back remarks from volunteers of the nutraceutical product(s)

| | |
|---|---|
| 1. Product Volunteered to take: | Herbal health protective and promotive Nutraceutical for Diabetics |
| 2. Age group: | 30–70 years (both men & women) |

TABLE 4-continued

Trial feed back remarks from volunteers of the nutraceutical product(s)

| | |
|---|---|
| 3. Number of Volunteers: | 10 in each case (8 men & 2 women) |
| 4. Profession/Family background: | Service class, business, retired & house wife etc |
| 5. Taste & flavor: | Acceptable |
| 6. Feeling after Consuming the Product: | |

After one week, two weeks & one month

| Product | One Week | Two Weeks | One Month | Conclusion |
|---|---|---|---|---|
| 1 | NS | NS | NS | NS (10)* |
| 2 | NS | NS | NS | NS (10) |
| 3 | NS | NS | Satisfactory | NS (10) |
| 4 | Satisfactory | Satisfactory | Good | Satisfactory (9) |
| 5 | Satisfactory | Good | Good | Good (7) |
| 6 | Good | Very Good | Very Good | Very Good (6) |
| 7 | Good | Very Good | Very Good | Very Good (7) |
| 8 | Very Good | Very Good | Very Good | Very Good (8) |
| 9 | Very Good | Excellent | Excellent | Excellent (8) |
| 10** | Very Good | Excellent | Excellent | Excellent (8) |
| 11** | Excellent | Excellent | Excellent | Excellent (8) |

NS = not significant effect, can not say;
*Number of persons who remarked out of ten;
**The products generated as final products;
The word satisfactory, good, very good and excellent stands for the efficacy of the product(s) as reported by volunteers after consuming the product(s), e.g. no side effects, no any kind of digestive problem, improvement in vigour, energetic, general health, and diabetes related health problems.

TABLE 4-continued

Trial feed back remarks from volunteers of the nutraceutical product(s)

The concluding remarks of the volunteers include the effect of nutraceutical product to control Blood/Urine Sugar Level, to ameliorate diabetes related health problems like fatigue, weakness, drowsiness, numbing effect, frequent urination, unusual thirst & hunger, weight loss, blurred vision, frequent skin infections and slow healing of wounds or sores.

Products 1–11 = Base (Roasted seed powders mixture) + extract of single herb/medicinal plant or different combinations.

Product 1 = Base + *Gymnema sylvestre*;

Product 2 = Base + *Gymnema sylvestre* + *Momordica charantia*;

Product 3 = Base + *Gymnema sylvestre* + *Momordica charantia* + *Syzgium cumini*;

Product 4 = Base + *Gymnema sylvestre* + *Momordica charantia* + *Syzgium cumini* + *Pterocarpus marsupium*;

Product 5 = Base + *Gymnema sylvestre* + *Momordica charantia* + *Syzgium cumini* + *Pterocarpus marsupium* + *Trigonella foenum-graecum*;

Product 6 = Base + *Gymnema sylvestre* + *Momordica charantia* + *Syzgium cumini* + *Pterocarpus marsupium* + *Trigonella foenum-graecum* + *Cinnamomum tamala*;

Product 7 = Base + *Gymnema sylvestre* + *Momordica charantia* + *Syzgium cumini* + *Pterocarpus marsupium* + *Trigonella foenum-graecum* + *Cinnamomum tamala* + *Withania somnifera*;

Product 8 = Base + *Gymnema sylvestre* + *Momordica charantia* + *Syzgium cumini* + *Pterocarpus marsupium* + *Trigonella foenum-graecum* + *Cinnamomum tamala* + *Withania somnifera* + *Pueraria tuberosa*;

Product 9 = Base + *Gymnema sylvestre* + *Momordica charantia* + *Syzgium cumini* + *Pterocarpus marsupium* + *Trigonella foenum-graecum* + *Cinnamomum tamala* + *Withania somnifera* + *Pueraria tuberosa* + *Asparagus racemosus*;

Product 10 = Base + *Gymnema sylvestre* + *Momordica charantia* + *Syzgium cumini* + *Pterocarpus marsupium* + *Trigonella foenum-graecum* + *Cinnamomum tamala* + *Withania somnifera* + *Pueraria tuberosa* + *Asparagus racemosus* + *Boerhaavia diffusa*;

Product 11 = Base + *Gymnema sylvestre* + *Momordica charantia* + *Syzgium cumini* + *Pterocarpus marsupium* + *Trigonella foenum-graecum* + *Cinnamomum tamala* + *Withania somnifera* + *Pueraria tuberosa* + *Asparagus racemosus* + *Boerhaavia diffusa* + *Aegle marmelos*.

Suggestions: Improvement in taste, solubility/suspension

TABLE 5

Trial Feed Back from Volunteers after consuming the Herbal health protective and promotive Nutraceutical(s) for Diebetics for 3 months.

| Sl. No. | Category | Age Group | Male | Female | Total Number of Volunteers | Remarks |
|---|---|---|---|---|---|---|
| 1. | IDDM | 4–10 | 5 | 5 | 10 (10*) | NS** |
| 2. | IDDM | 20–50 | 2 | 8 | 10 (5*) | Satisfactory |
| 3. | IDDM | 50–75 | 5 | 5 | 10 (7*) | Good |
| 4. | NIDDM | 30–40 | 20 | 10 | 30 (24*) | Excellent |
| 5. | NIDDM | 40–50 | 20 | 10 | 30 (21*) | Excellent |
| 6. | NIDDM | 50–85 | 20 | 10 | 30 (21*) | Excellent |

Age Group in years,
*Number of persons remark,
NS = Not satisfactory,
**did not continue due to its taste Doses: 5 to 10 g (depending on age & symptoms) of the nutraceutical (Nutra-Diab) was taken twice a day before breakfast/lunch and dinner, as food supplement beside the normal/usual drug/medicine/insulin doses etc. being used by the patient/person.

The invention claimed is:

1. A herbal nutraceutical formulation for diabetics, the formulation consisting essentially of:
   50–90% by wt. of seed products selected from the group consisting of legumes, cereals, and pseudocereals; and
   10–50% by wt of a plant product composition consisting of herbs and medicinal plants,
   wherein the plant product composition consists essentially of 2–40% by wt. *Gymnema sylvestre*, 2–40% by wt. *Momordica charantia*, 2–40% by wt. *Syzgium cumini*, 2–40% by wt. *Pterocarpus marsupium*, 2–40% by wt. *Trigonella foenum-graecum*, 2–40% by wt. *Cinnamomum tamala*, 0–20% by wt. *Withania somnifera*, 0–20% by wt. *Coccinia indica*, 0–20% by wt. *Pueraria tuberosa*, 0–20% by wt. *Asparagus recemosus*, 0–20% by wt. *Boeraavia diffusa*, 0–20% by wt. *Aegle marmelos*, and, optionally, acceptable amounts of additives selected from the group consisting of *Piper longum, Chlorophytum tuberosum, Curcuma longa,* and *Elettaria cardamomum*.

2. A herbal formulation as claimed in claim 1, wherein said plant product composition consists essentially of 2–40% by wt. *Gymnema sylvestre*, 2–40% by wt. *Momordica charantia*, 2–40% by wt. *Syzgium cumini*, 2–40% by wt. *Pterocarpus marsupium*, 2–40% by wt. *Trigonella foenum-graecum* and 2–40% by wt. *Cinnamomum tamala*.

3. A herbal formulation as claimed in claim 1, wherein said plant product composition consists essentially of 2–40% by wt. *Gymnema sylvestre*, 2–40% by wt. *Momordica charantia*, 2–40% by wt. *Syzgium cumini*, 2–40% by wt. *Pterocarpus marsupium*, 2–40% by wt. *Trigonella foenum-graecum* 2–40% by wt. *Cinnamomum tamala*, and *Withania somnifera*.

4. A herbal formulation as claimed in claim 1, wherein said plant product composition consists essentially of 2–40% by wt. *Gymnema sylvestre*, 2–40% by wt. *Momordica charantia*, 2–40% by wt. *Syzgium cumini*, 2–40% by wt. *Pterocarpus marsupium*, 2–40% by wt. *Trigonella foenum-graecum* 2–40% by wt. *Cinnamomum tamala*, *Withania somniferai* and *Pueraria tuberosa*.

5. A herbal formulation as claimed in claim 1, wherein said plant product composition consists essentially of 2–40% by wt. *Gymnema sylvestre*, 2–40% by wt. *Momordica charantia*, 2–40% by wt. *Syzgium cumini*, 2–40% by wt. *Pterocarpus marsupium*, 2–40% by wt. *Trigonella foenum-graecum* 2–40% by wt. *Cinnamomum tamala*, *Withania somniferai*, *Pueraria tub erosa*, and *Asparagus recemosus*.

6. A herbal formulation as claimed in claim 1, wherein said plant product composition consists essentially of 2–40% by wt. *Gymnema sylvestre*, 2–40% by wt. *Momordica charantia*, 2–40% by wt. *Syzgium cumini*, 2–40% by wt. *Pterocarpus marsupium*, 2–40% by wt. *Trigonella foenum-graecum* 2–40% by wt. *Cinnamomum tamala*, *Withania somniferai*, *Pueraria tuberosa*, *Asparagus recemosus*, and *Boeraavia diffusa*.

7. A herbal formulation as claimed in claim 1, wherein said plant product composition consists essentially of 2–40% by wt. *Gymnema sylvestre*, 2–40% by wt. *Momordica charantia*, 2–40% by wt. *Syzgium cumini*, 2–40% by wt. *Pterocarpus marsupium*, 2–40% by wt. *Trigonella foenum-graecum* 2–40% by wt. *Cinnamomum tamala*, *Withania somniferai*, *Pueraria tuberosa*, *Asparagus recemosus*, *Boeraavia diffusa*, and *Aegle marinelos*.

8. A herbal formulation as claimed in claim 1, wherein the seed products are selected from the group consisting of dried seeds, roasted seeds, and powdered seeds.

9. A herbal formulation as claimed in claim 1, wherein the legumes are selected from the group consisting of *Glycine max, Cicer arietinum, Phaseolus mungo, Cyamompsis tetragonoloba*, and mixtures thereof.

10. A herbal formulation as claimed in claim 1, wherein the cereal is *Hordeum vulgare*.

11. A herbal formulation as claimed in claim 1, wherein the pseudocereals are selected from the group consisting of *Amaranthus hypochondriacus* and *Fagopyrum esculantum*.

12. A herbal formulation as claimed in claim 1, wherein the said herb and medicinal plant products are plant parts selected from the group consisting of roots, fruits, seeds, leaves, wood, and whole plants.

13. A herbal formulation as claimed in claim 1, wherein said plant product composition contains the additives selected from the group consisting of *Piper longum, Chlorophytum tuberosum, Curcuma longa,* and *Elettaria cardamomum*.

14. A herbal formulation as claimed in claim 1, in which the legume is *Cicer arietnum* and the pseudocereal is *Fagopyrum esculantum*.

15. A herbal formulation as claimed in claim 1, wherein said seed products comprise 3–80% by wt. legumes, 5–40% by wt. cereals, and 10–30% by wt. pseusocereals.

16. A herbal formulation as claimed in claim 1, wherein said formulation is prepared by a process comprising the steps of:
   obtaining powder or extract of the herbs and medicinal plants;
   drying the extract to obtain a residue; and
   mixing the residue with the seed products.

17. A herbal formulation as claimed in claim 16, wherein said plant product composition is prepared by a process comprising the steps of:
   a) crushing or powdering the herb and medicinal plants;
   b) extracting the crushed or powdered herb and medicinal plants with aqueous alcohol in the range of 5 to 95% v/v water to alcohol for 5 to 48 hours at a temperature of 20 to 50° C.; and
   c) removing said alcohol under reduced pressure at 20 to 80° C. to form the plant product composition.

18. A herbal formulation as claimed in claim 1, wherein said plant product composition is prepared by a process comprising the steps of:
   a) crushing or powdering the herb and medicinal plants;
   b) extracting the crushed or powdered herb and medicinal plants with aqueous alcohol in the range of 5 to 95% v/v water to alcohol for 5 to 48 hours at a temperature of 20 to 50° C.; and c) removing said alcohol under reduced pressure at 20 to 80° C. to form the plant product composition.

19. A herbal formulation as claimed in claim 18, wherein step b) is carried out three times; and the resulting alcohol extracts are combined prior to step c).

20. A herbal formulation as claimed in claim 19, wherein said alcohol is selected from the group consisting of methanol, ethanol, iso-propanol, and butanol.

21. A herbal formulation as claimed in claim 18, wherein said plant product composition contains plant products of *Boerhaavia diffusa*.

22. A herbal formulation as claimed in claim 21, wherein said plant product composition contains plant products of *Aegle marmelos*.

* * * * *